United States Patent [19]
Moulton et al.

[11] Patent Number: 5,483,068
[45] Date of Patent: Jan. 9, 1996

[54] USE OF IR (THERMAL) IMAGING FOR DETERMINING CELL DIAGNOSTICS

[76] Inventors: Russell D. Moulton, 6316 Felder Dr., San Jose, Calif. 95123; Benjamin Chaloner-Gill, 520 Mansion Ct., #303, Santa Clara, Calif. 95054

[21] Appl. No.: 178,943

[22] Filed: Jan. 7, 1994

[51] Int. Cl.⁶ .............................. G01J 5/00; G01N 25/72; H01M 10/48
[52] U.S. Cl. .................. 250/340; 250/338.1; 374/45; 374/124; 374/129; 429/91
[58] Field of Search .................. 429/90, 91; 250/342, 250/340, 338.1, 334; 374/45, 124, 129

[56] References Cited

U.S. PATENT DOCUMENTS

| | | |
|---|---|---|
| 3,978,281 | 8/1976 | Burrer . |
| 4,009,052 | 2/1977 | Whittingham . |
| 4,118,550 | 10/1978 | Koch . |
| 4,347,530 | 8/1982 | Stetson . |
| 4,830,939 | 5/1989 | Lee et al. . |
| 4,990,413 | 2/1991 | Lee et al. . |
| 5,037,712 | 8/1991 | Shackle et al. . |
| 5,065,024 | 11/1991 | McCullough . |
| 5,229,225 | 7/1993 | Shackle . |

OTHER PUBLICATIONS

Measurement Systems Application and Design, Doebelin, (no month) 1983, pp. 646–650.

*Primary Examiner*—John S. Maples

[57] ABSTRACT

In a new method, a defective electrochemical cell is detected by non-invasive means before assembly into a battery comprising multiple cells. The method detects faulty cells by sensing and detecting variations in the intensity level of infrared radiation emitted from an exterior surface of the cell or battery. The scanning and detection, preferably, is conducted by sensing infrared energy in a range of about 2 to about 12 um (microns) emitted from the major surface of the cell or battery. The variations are recorded as a function of geometric variables indicative of the geographic position of the variations.

7 Claims, 3 Drawing Sheets

USE OF IR (THERMAL) IMAGING FOR DETERMINING CELL DIAGNOSTICS

FIELD OF THE INVENTION

This invention relates to a method and system for detecting faulty operating electrochemical cell components and, in particular, to the detection of short circuits across an electrolyte layer between an anode and a cathode of power generation or storage electrochemical cells.

BACKGROUND OF THE INVENTION

Electrochemical devices employing thin layer electrodes such as lithium electrodes are the subject of intense investigation. Typical electrochemical devices or batteries include a metal (lithium) anode, a transition metal oxide composite cathode, and an electrolyte which is typically a solid or liquid and which includes a dissolved metal salt. These new batteries all rely on the technology based on thin films where energy is stored in compact devices. This has lead to the need to produce thinner and thinner electrode and electrolyte layers. The utilization and handling of such layers becomes more difficult as they become thinner. Typical thin film electrodes and electrolytes are easily damaged during manufacturing when such film layers are assembled to form a cell. Multiple cells are assembled to form batteries. During manufacture and assembly, some layers may become punctured permitting direct contact through the electrolyte layer between the anode and cathode. This causes a short circuit rendering the cell defective. Any battery containing a defective cell is itself defective. Under common usage, the term "battery" is often applied to a single cell having an anode, a cathode and an electrolyte layer, as well as to multiple cells.

It is necessary to test the open circuit voltage (OCV) of each cell immediately after it is made in order to determine if it is defective. This is only practical when a small number of cells are made, as for laboratory evaluation. The OCV for a given cell is compared to that of other cells, usually within the same lot, and also compared to the historical norm for previously made cells. Cells that exhibit an uncharacteristically low OCV are thought to have a short circuit, meaning that there is contact between the cathode and anode across the electrolyte layer. If the OCV continues to drop over time, a short circuit becomes the most probable reason. Such OCV testing is not practical for volume production of batteries. However, in order to have an effectively performing battery, it is necessary that such battery not contain any defective cells, that is, cells having short circuits. In present high volume manufacturing, large numbers of cells are produced then immediately assembled into a battery. Batteries having defective cells are later discovered and disposed of, leading to unnecessary waste.

What is needed is a new method to detect defective cells which is applicable to high volume production; which is a non-destructive method to detect faulty or defective cells: and which overcomes problems of including such defective cells in a battery.

SUMMARY OF THE INVENTION

According to the invention, there is provided a method for determining when a battery or cell is faulty. In accordance with common usage, a battery consists of one or more individual cells. A cell comprises an anode, a cathode, and an electrolyte therebetween. The method detects faulty cells by sensing and detecting variations in the intensity level of infrared radiation emitted from an exterior surface of the cell or battery. The scanning and detection, preferably, is conducted by sensing infrared energy in a range of about 2 to about 12 μm (microns) emitted from the major surface of the cell or battery. The variations are recorded as a function of geometric variables indicative of the geographic position of the variations. More specifically, a major surface of an electrode, either the anode or cathode of the battery, is scanned to detect any regions of such major surface which have a higher intensity level of infrared radiation emitted as compared to other surrounding regions of the major surface of the electrode being scanned.

Alternatively, the detection method may rely upon scanning a mador surface of one of the electrodes of the cell to detect variations in the intensity level of infrared radiation as compared with a pre-established intensity of infrared radiation emitted by a normal electrode surface.

Accordingly, objects, features and advantages of the present invention are to provide an improved electrochemical battery without defective cells which maintains its integrity over a prolonged life cycle as compared to presently used batteries; and to provide an economical and effective method for identifying short circuits in such cells prior to their being assembled into a finished battery.

These and other objects, features and advantages will become apparent from the following description of the preferred embodiments, claims and accompanying drawings.

DETAILED DESCRIPTION OF THE PREFERRED EMBODIMENTS

The invention provides a method and infrared imaging system for sensing faulty electrochemical cells. Most of these systems have the function of providing a visual display in which the shades of color represent various temperature levels of the surface of some object (target) on which the infrared camera is focused. These shades of gray are related to infrared energy levels emitted from the target. Infrared temperature sensing requires knowledge of the emittance of the target surface to convert the detector signal to degrees of temperature.

INFRARED IMAGING SYSTEMS

Figure 1:
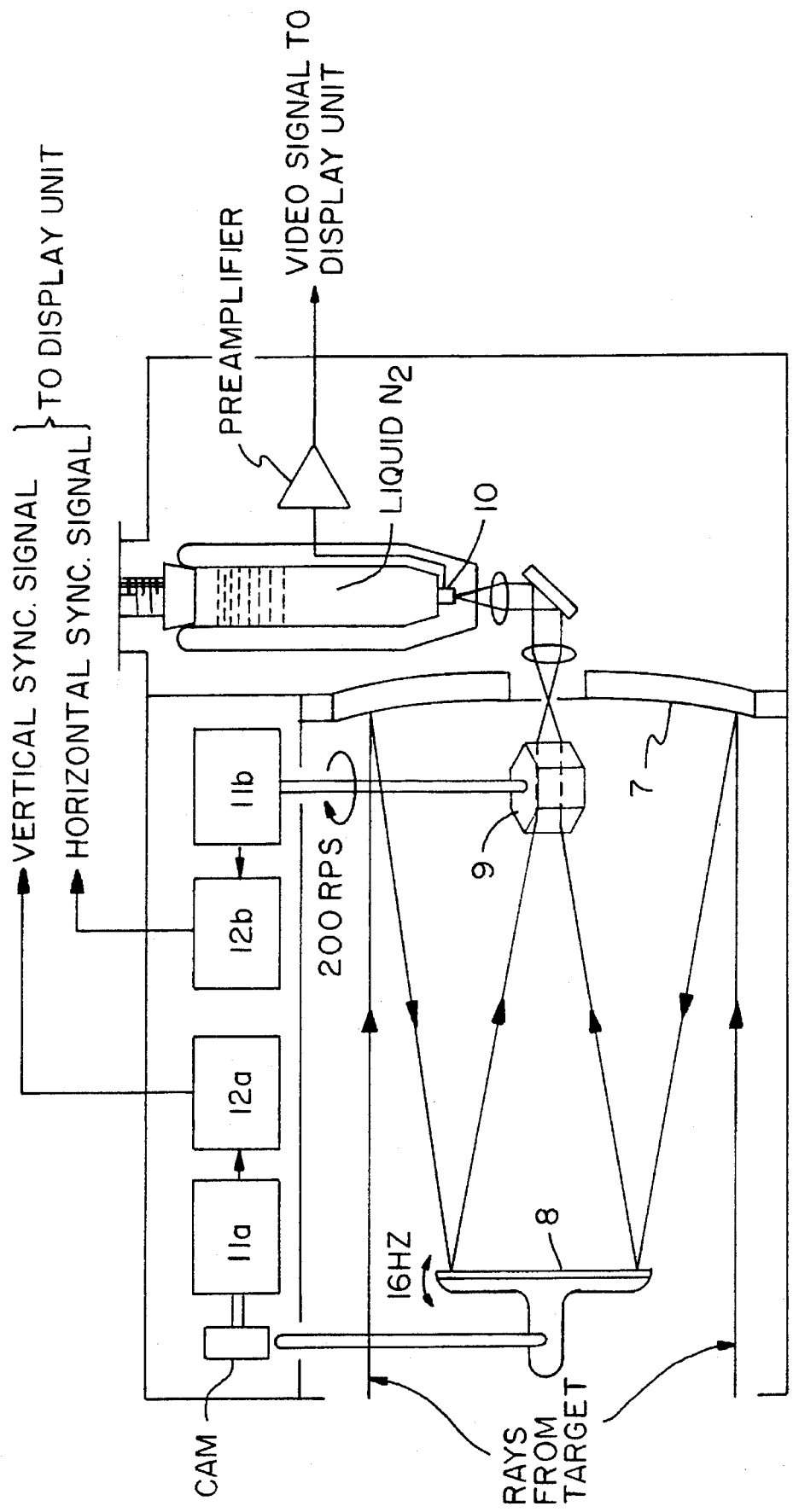
FIG. 1 is a schematic illustration of a basic infrared imaging system.
Figure 2:
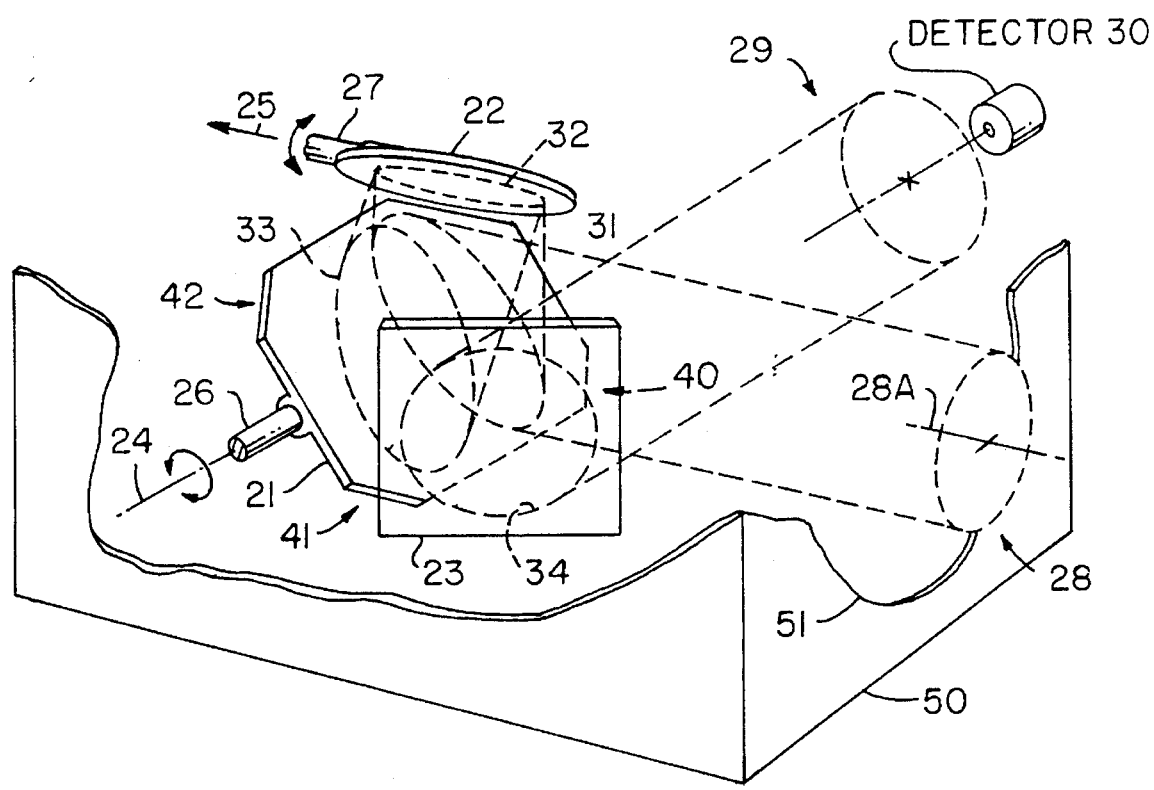
FIG. 2 is a perspective view of an illustrative two-dimensional scanning reflector mechanism of an infrared imaging system.

The general layout of a typical infrared imaging system is as shown in FIGS. 1 and 2. The principle of the system will be briefly described with reference to FIG. 1. The system is as illustrated in schematic form in FIG. 2. It is to be understood that such systems can be laid out in many geometries and that the schematic illustrations of FIGS. 1 and 2 are intended to be exemplary.

To provide compatibility with standard television-type raster scan displays, typically a two-dimensional imaging system is used for receiving radiant energy. The imaging system usually includes a scanner, which is a device containing a number of reflectors to direct radiant energy from successive elemental areas of an input field of view to one or more radiant energy detectors. Although a single, gimballed reflector might be used to scan the desired field of view, two orthogonal reflectors are generally used, with each reflector being separately driven about a single axis.

For serial scanning, one or both of the reflectors may be oscillated about an axis; or one axis may be scanned by using mechanisms such as a multifaceted polygonal mirror, sawtooth reflective wheel, or internally reflective carousel mounted on a high revolution-per-minute (RPM) motor.

FIG. 1 illustrates a system where scanning of the target surface is accomplished by focusing the radiation on a spherical mirror 7 and then a plane mirror 8 oscillating about a horizontal axis at 16 Hz. This scans the line of sight vertically over the target surface. The image from the plane mirror 8 is focused on an eight-sided prism 9 (rotating at 200 r/s) which provides the horizontal scanning and results in a "picture" with a frame rate of 16 frames/s and 100 lines per picture. An indium antimonide (InSb) detector 10 (cooled by liquid nitrogen to reduce its noise level produces an electrical signal proportional to the incident radiant flux. To produce a thermal image of the target on a TV picture tube, horizontal and vertical deflection signals are picked off the scanning-system motor shafts 11a, 11b and photocells 12a, 12b to position the electron beam, while the infrared detector signal (video signal) modulates the beam intensity. Thus the TV tube displays a 100-line picture whose local intensity (shades of color) represents target temperature.

Using suitable optics, infrared scanners can produce full-scale thermal images of objects as small as 0.6 mm$^2$ at an 8-mm working distance with a "spot size" of 0.01 mm. Temperature differences as small as 0.1° C. can be resolved for a target at 30° C. Of course, larger targets may be scanned by increasing the working distance; a typical 5'×5' field of view gives a target size of 8.8×8.8 m at a range of 100 m. A typical "thermogram" has a calibrated gray scale "temperature" from black to white with digits corresponding to the gray scale. Another useful display mode (not shown) shows isotherms (lines of constant temperature) as bright lines on the thermogram. A further refinement gives a 10-color display of isotherms, with each color being associated with a different known temperature.

The noncontacting nature of the sensing method, together with the display of the entire surface-temperature distribution over an object, gives infrared imaging systems unique application possibilities. FIG. 2 illustrates a system as described in U.S. Pat. No. 4,347,530; other systems are described in U.S. Pat. Nos. 5,065,024 and 3,978,281, each of the three patents is incorporated by reference herein in its entirety. Each of the aforesaid patents is assigned to Inframetrics, Inc. which provided an imaging scanner sold under the designated Model 760 Inframetrics Infrared Thermal Imaging Radiometer. A similar model was used in the examples of the method described later.

As shown in FIG. 2, a bundle of radiant energy 28 from an object travels along a first optical path 28 and strikes the vertical-scan reflector 21. As the reflector 21 oscillates (FIG. 2), the axis 28a of ray bundle 28 scans an elemental area of an object scene and for a fixed angular position of reflector 22, remains essentially at a constant angle relative to the axis 24 of the reflector 21. An opening 51 in the housing 50 of the scanning mechanism together with lenses or windows that might be placed in that opening constitutes the area within which radiant energy bundle 28 moves in a raster fashion. An outline of the circular bundle traveling along the axis 28a forms what is characterized as "footprint" 31 on the surface of reflector 21. That same circular bundle is then directed to horizontal-scan reflector 22 along another axis and establishes a second footprint 32 on the surface thereof. As the horizontal reflector 22 oscillates, the axis 20 of the ray bundle is always perpendicular to the axis 25 of the horizontal reflector 22. The bundle being reflected at footprint 32 is directed back onto the surface of reflector 21 along still another axis and forms yet a third skewed, or oblong, footprint 33 thereon. In the embodiment shown, the bundle then is directed from reflector 21 onto the surface of the fixed, or folding, reflector 23, which is angularly positioned so as to ultimately direct the bundle to a detector element 30. A footprint 34 marks the impression of the circular bundle on folding reflector 23 which directs the bundle along a second optical path 29 that lies in a path different from the path of the bundle of the first optical path 28. Optical path 29 may also include an objective lens assembly comprising a single lens or lenses which focus the ray bundle onto a detector 30, which may be an array of detector elements, also lying in optical path 29.

In operation, as reflector 22 pivots about its axis 25, footprint 31 moves in a direction parallel to axis 24 of reflector 21, thereby establishing a minimum "horizontal-width" required of reflector 21, in conjunction with the essentially stationary footprint 33. Because the axis of optical paths 28 and 29 lie along different paths, the axis 25 of the horizontal scan reflector 22 must be positioned so that it does not obstruct the optical bundle 28 as the vertical-scan reflector 21 pivots about its axis 24. To best accommodate this requirement, the nominal angle about which the vertical-scan reflector 21 is disposed is selected with respect to the optical axis 28a. This permits the reflectors 21 and 22 to be placed close together. Furthermore, axis 25 is perpendicular to axis 20 so as to provide a scanning pattern that is compatible with the scanning pattern of a conventional television display monitor.

The imaging scanner is used to scan along a major surface of an electrode of an electrochemical cell. It is possible to scan either the anode or cathode side of such a cell. A brief description of a conventional cell will now be provided to facilitate understanding of the process for sensing faults in such cells.

Cell to be Analyzed

Figure 3:
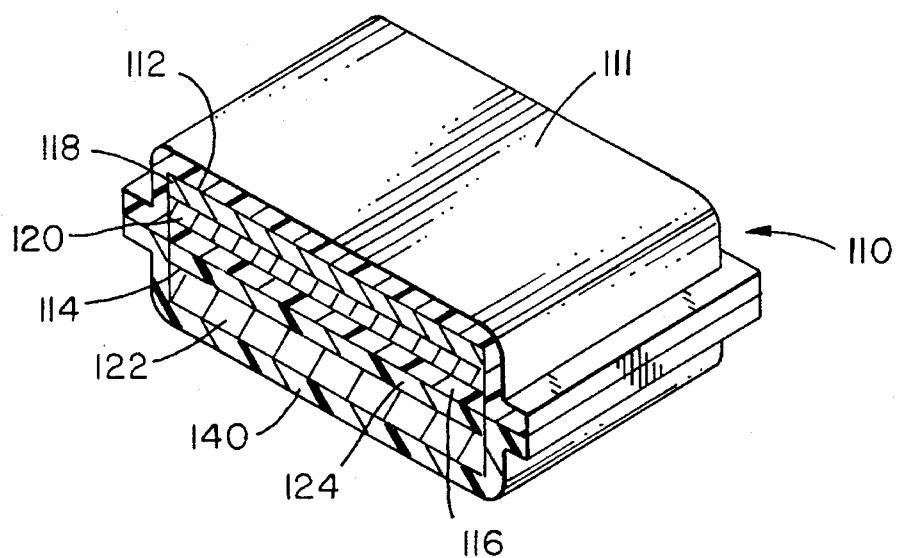
FIG. 3 is an illustration of a cross-section of a thin battery or cell embodying the invention.

As shown in the drawings, an electrochemical cell or battery 110 has a negative electrode side 112, a positive electrode side 114, and an electrolyte 116 (FIG. 3). In accordance with common usage, a battery may consist of a single cell or multiple cells. The negative electrode is the anode during discharge, and the positive electrode is the cathode during discharge. The negative electrode side includes current collector 118, typically of nickel, stainless steel, and/or copper foil, and a body of negative electrode material 120. The negative electrode material 120 is sometimes simply referred to as the negative electrode or negative electrode composition. The negative electrode side 112 may consist of only a metallic electrode 120 without a separately distinguishable current collector 118. The positive electrode side 114 includes current collector 122, typically of aluminum, nickel, stainless steel, and/or copper foil, or such foils having a protective conducting coating foil, and a body of positive electrode material 124. The cathode composition 124 and current collector 1122 will be more specifically described below. Positive electrode material 124 is sometimes simply referred to as the positive electrode or positive electrode composition. The electrolyte 116 is typically a solid or liquid electrolyte. Suitable liquid or solid electrolytes are known, with polymer electrolytes presently being preferred are described in U.S. Pat. Nos. 4,009,052, 4,118, 550, 4,792,504 4,830,939, 4,990,413, 5,037,712 and 5,229, 225 each of which is incorporated herein by reference in its entirety. In one embodiment, the electrolyte is a solid organic polymer matrix containing an ionically conducting powder or liquid with an alkali metal salt and the liquid is an aprotic polar solvent. Cell 110 also includes a protective covering 140 in the form of a sealed container 140.

During manufacture, the current collector, cathode composition and electrode composition are typically prepared in a series of layers with the cathode composition being first applied to the current collector and then the electrolyte composition applied to the cathode composition. Next, an anode composition is applied to a current collector and then the cell is assembled with the layers arranged as follows: current collector, cathode composition, electrolyte composition, anode composition, current collector. The assembly is then inserted into an air and water impermeable protective material and the edges of the protective material are sealed, preferably by heat sealing around edges of the cell components. Sealing preferably occurs under vacuum conditions to enable the protective material to form a sealed container 140 around the component layers and electrodes such that the only external access to the component layers is via the electrodes. (FIG. 3)

Since the cell components are highly reactive, they must be kept in an environment having reduced oxygen and water content. This means that the non-destructive method for detecting faults preferably occurs by examining the exterior of the protective covering 140 to determine a fault condition in the cell 110. In the practice of the method for detecting faults, some adjustment may be necessary based on the material of construction of the cell covering 140.

Heat sealable gas and water permeable protective materials form multi-layered covering 140. The covering 140 has an interior heat sealable layer comprising ethylene acrylic acid copolymer, an intermediate barrier layer comprising aluminum foil, and an exterior layer of polyethylene terephthalate (PET, Mylar). And other heat sealable protective composites have the following layers: nylon, (polyamide polymer), polyethylene (adhesive), aluminum foil, polyethylene, nylon, polyethylene, and Surlyn (ionomer resin containing metallic elements). Still another such composite has layers of Mylar, polyethylene, aluminum foil and Surlyn. Commercially available heat sealable materials of the types described above can have an overall thickness of less than 200 microns. The method of the invention permits scanning to be conducted through the covering 140 to detect faults in the cell 110. This is possible because the cell 110 has a planar arrangement and each electrode side 112,114 has a flat major surface 111. Infrared imaging of a major surface 111 detects variations in the intensity level of infrared radiation emitted from such surface in a range of about 2 to about 12 $\mu m$ (microns). Such energy is recorded as a function of geometric variables indicative of geographic position of such variation. Although it is preferred to provide a scan showing variations in infrared energy level as a function of specific geometric variables in a raster array, it is also possible to detect hot spots of an electrode or cell by scanning the major surface to simply detect regions of the major surface which have a higher intensity level as compared to other regions of the major surface. This can be done without the need to pinpoint in detail the locations of hot spots. The purpose of such a scan is to merely identify whether a cell has hot spot regions, rather than determining the precise location of such hot spot regions.

In still another variation of the method, the major surface of an electrode is scanned to detect variations in the intensity level of infrared as compared with a pre-established intensity of infrared radiation emitted by a normal electrode in a cell not having hot spots.

Regardless of the specific method chosen, the invention provides the ability to obtain a thermogram which will show the occurrence of a self-discharging cell because such cell will have a higher temperature or regions of higher temperature than a stable non-self-discharging cell. This depends on the principle that a battery or cell that is short circuited or allowed to discharge as fast as it can, will tend to heat up. Therefore, the actual short circuit locations or regions within the cell appear as hot spots on the thermogram to further characterize the defect. The method of the invention provides the advantage of detecting cells with hot spots so that they may be discarded promptly before being assembled into a battery. Those skilled in the art will appreciate that the method of the invention could also be used to investigate electrochemical and physical processes inside of the cell during repeated discharging/charging cycles. Unequal topological distribution of electrochemical activity is likely to manifest itself as relative warm and cool zones or regions.

It has been found that a suitable device for conducting the method of the invention is an infrared thermal imaging radiometer sold by Inframetrics of Boston, Ma. under the designation Model 760. This imaging device has a horizontal field of view of 20° and a vertical field of view of 15°. It has 194 resolution elements per line and an image field rate of about 60 Hertz (Hz). It has a focus range of several inches or centimeters to infinity and an IR line rate of 7,000 to 8,000 Hz. It has an ability to measure temperature in a range of −20° C. to 400° C. (−4° to 752° F.); and an extended range of 20° C. to 1,500° C. (68° to 2732° F.). It has an HgCdTe detector with a spectral range of as high as 3 to 12 microns ($\mu m$).

Example

The inframetric 760 Hg-Cd-Te detector model was used to analyze heat developed inside laboratory prepared cells during aggressive discharges. Cells were discharged by short-circuit, by self-discharge through 1 and 10 ohm resistors, and using 10 mA/cm$^=$ constant currents. In the case of the 10 mA/cm$^2$ constant current discharge, the current varied by no more than about 10% from a desired value and typically varied by no more than about 5%. Infrared energy was detected in a range of about 2 to about 12 um (microns). Temperature excursions of greater than 10° C. were measured for some of the short-circuit tests. (The measurements actually went off scale after the 10° C. expected span was exceeded.) However, a constant current discharge of 4 mA/cm$^2$ did not reveal any "hotspots". The model 760's limit of detection of differences in temperature is 0.2° C. In order to locate problem spots in cells suspected of having soft-shorts it was necessary to make adjustments due to the aluminum-core packaging material used. Such material is thermally reflective and required application of adhesive-backed paper labels to the exterior surface of the cell to improve the infrared emissivity of the surface.

Figure 4:
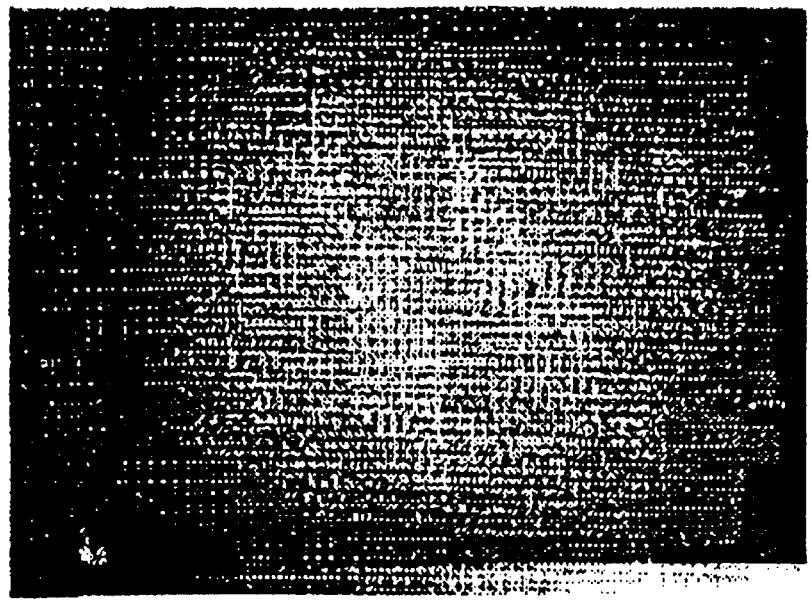
FIGS. 4 and 5 are copies of monochrome printouts of a computer data file produced, but not interpreted, by thermal imaging software.
Figure 5:
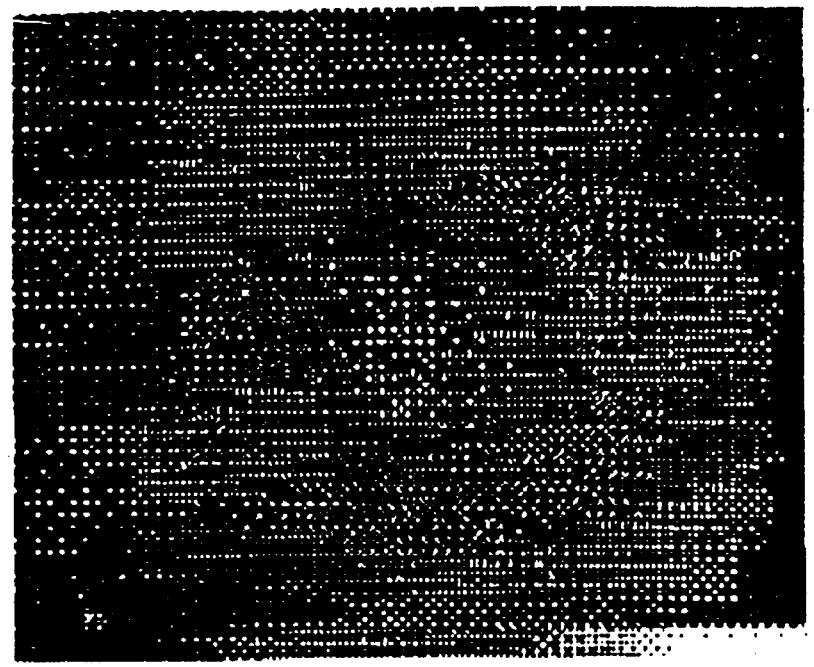

FIGS. 4 and 5 are copies of monochrome printouts made from a computer file stored, but not reinterpreted for the printer, by the thermal imaging software. FIG. 4 shows a lab cell with adhesive labels applied to the majority of the surface, in which the differences in surface reflectivity is visible. The image of FIG. 5 more clearly shows thermal differences in the interior of the cell.

While this invention has been described in terms of certain embodiments thereof, it is not intended that it be limited to the above description, but rather only to the extent set forth in the following claims.

The embodiments of the invention in which an exclusive property or privilege is claimed are defined in the appended claims.

We claim:

1. A method for determining when an electrochemical cell or battery is faulty comprising scanning and detecting variations in the intensity level of infrared radiation emitted from an exterior major surface of the battery or cell, coextensive with a major surface of an electrode of such cell, said scanning and detecting conducted by sensing infrared energy in a range of about 2 to about 12 μm (microns) emitted from the exterior surface.

2. The method according to claim 1 and further comprising recording said variations as a function of geometric variables indicative of the geographic position of such variations on the exterior surface.

3. The method according to claim 1 and further comprising scanning the exterior surface to detect said variations in the intensity level of infrared radiation of the exterior surface as compared with the intensity of infrared radiation emitted by an exterior major surface of another cell which is not defective.

4. A method for determining when an electrochemical cell or battery is faulty comprising:
   a) initially thermally stabilizing the cell to be fault tested;
   b) discharging the cell at a current which is relatively constant and varies by no more than about 10% during discharge:
   c) scanning to detect infrared response during or immediately after such discharge by scanning and detecting variation in the intensity level of infrared radiation emitted from an exterior major surface of the battery or cell, co-extensive with a major surface of an electrode of such cell, said scanning and detecting conducted by sensing infrared energy in a range of about 2 to about 12 μm (microns) emitted from the exterior surface.

5. The method according to claim 4 and further comprising recording said variations as a function of geometric variables indicative of the geographic position of such variations on the exterior surface.

6. The method according to claim 4 and further comprising scanning the exterior surface to detect said variations in the intensity level of infrared radiation of the exterior surface as compared with the intensity of infrared radiation emitted by an exterior major surface of another cell which is not defective.

7. The method according to claim 4 wherein the current varies by no more than about 5%.

* * * * *